(12) United States Patent
Siedenburg

(10) Patent No.: US 11,357,415 B2
(45) Date of Patent: *Jun. 14, 2022

(54) LIGHT-BASED NON-INVASIVE BLOOD PRESSURE SYSTEMS AND METHODS

(71) Applicant: Stryker Corporation, Kalamazoo, MI (US)

(72) Inventor: Clinton T. Siedenburg, Everett, WA (US)

(73) Assignee: Stryker Corporation, Kalamazoo, MI (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/167,195

(22) Filed: Oct. 22, 2018

(65) Prior Publication Data

US 2019/0125191 A1 May 2, 2019

Related U.S. Application Data

(60) Provisional application No. 62/577,982, filed on Oct. 27, 2017.

(51) Int. Cl.
*A61B 5/02* (2006.01)
*A61B 5/022* (2006.01)
(Continued)

(52) U.S. Cl.
CPC ............ *A61B 5/022* (2013.01); *A61B 5/0075* (2013.01); *A61B 5/0261* (2013.01);
(Continued)

(58) Field of Classification Search
CPC ... A61B 5/022; A61B 5/02108; A61B 5/0075; A61B 5/0261; A61B 2562/0233;
(Continued)

(56) References Cited

U.S. PATENT DOCUMENTS

| 4,336,808 A | 6/1982 | Ohno et al. |
| 5,249,577 A | 10/1993 | Shinomura et al. |

(Continued)

FOREIGN PATENT DOCUMENTS

| EP | 0898938 A2 | 3/1999 |
| WO | WO2008050334 A2 | 5/2008 |

(Continued)

OTHER PUBLICATIONS

O'Rourke et al., "Vascular impedance in studies of arterial and cardiac function", Physiol Rev. Apr. 1982;62(2):570-623.

(Continued)

*Primary Examiner* — Rex R Holmes
(74) *Attorney, Agent, or Firm* — Lee & Hayes, P.C.

(57) ABSTRACT

Light-based non-invasive blood pressure measurement systems and methods that include a sensor having a light emitter and a light detector are disclosed. The light emitter emitting coherent or non-coherent light that is transmitted into and reflected from the tissues of the patient, including reflecting from moving blood. The light reflected from the moving blood being having a Doppler shift and detected by the light detector to generate a non-invasive blood pressure signal. The non-invasive blood pressure signal is processed to determine the instantaneous velocity of the blood. Additionally, pulse wave velocity data is obtained nearly, or substantially, simultaneously with the acquisition of the non-invasive blood pressure signal. Using the pulse wave velocity, the instantaneous velocity of the blood and a density of the blood, an instantaneous blood pressure can be determined.

21 Claims, 6 Drawing Sheets

(51) Int. Cl.
  *A61B 5/00* (2006.01)
  *A61B 5/026* (2006.01)
  *A61B 5/021* (2006.01)

(52) U.S. Cl.
  CPC ...... *A61B 5/02108* (2013.01); *A61B 5/02007* (2013.01); *A61B 5/02141* (2013.01); *A61B 5/6825* (2013.01); *A61B 5/725* (2013.01); *A61B 5/7225* (2013.01); *A61B 5/7278* (2013.01); *A61B 2562/0233* (2013.01)

(58) Field of Classification Search
  CPC . A61B 5/02141; A61B 5/7225; A61B 5/6825; A61B 5/7278; A61B 5/02007; A61B 5/725
  See application file for complete search history.

(56) References Cited

U.S. PATENT DOCUMENTS

| | | | |
|---|---|---|---|
| 5,309,916 | A | 5/1994 | Hatschek |
| 5,535,747 | A | 7/1996 | Katakura |
| 6,176,832 | B1* | 1/2001 | Habu .................. A61B 5/0285 600/485 |
| 6,261,233 | B1 | 7/2001 | Kantorovich |
| 6,419,632 | B1 | 7/2002 | Shiki et al. |
| 6,676,600 | B1 | 1/2004 | Conero et al. |
| 7,125,383 | B2 | 10/2006 | Hoctor et al. |
| 7,306,563 | B2 | 12/2007 | Huang |
| 7,621,876 | B2 | 11/2009 | Hoctor et al. |
| 7,815,574 | B2 | 10/2010 | Mourad et al. |
| 8,738,128 | B2 | 5/2014 | Pearce et al. |
| 9,161,701 | B2 | 10/2015 | Lading |
| 10,722,209 | B2 | 7/2020 | Chen et al. |
| 2002/0177781 | A1 | 11/2002 | Amano |
| 2005/0131282 | A1* | 6/2005 | Brodnick ............. A61B 5/4821 600/323 |
| 2005/0143640 | A1 | 6/2005 | Hoctor et al. |
| 2006/0211942 | A1 | 9/2006 | Hoctor et al. |
| 2007/0093702 | A1 | 4/2007 | Yu et al. |
| 2007/0167844 | A1 | 7/2007 | Asada et al. |
| 2011/0040197 | A1 | 2/2011 | Welch et al. |
| 2012/0123246 | A1 | 5/2012 | King et al. |
| 2014/0143064 | A1 | 5/2014 | Tran |
| 2014/0200423 | A1* | 7/2014 | Eisen ................. A61B 5/14552 600/340 |
| 2015/0073230 | A1 | 3/2015 | Stergiou |
| 2015/0238095 | A1 | 8/2015 | Lading et al. |
| 2015/0327785 | A1 | 11/2015 | Lading et al. |
| 2015/0327786 | A1 | 11/2015 | Lading et al. |
| 2016/0030758 | A1 | 2/2016 | Guiney et al. |
| 2016/0038117 | A1 | 2/2016 | Tamada |
| 2016/0095572 | A1 | 4/2016 | Aguren |
| 2016/0262639 | A1 | 9/2016 | Ukawa |
| 2016/0287095 | A1* | 10/2016 | Gu ......................... A61B 5/318 |
| 2016/0345930 | A1 | 12/2016 | Mizukami et al. |
| 2017/0000688 | A1 | 1/2017 | Kaufman et al. |
| 2017/0042504 | A1 | 2/2017 | Rich et al. |
| 2017/0172429 | A1 | 6/2017 | Takoh et al. |
| 2017/0273664 | A1 | 9/2017 | Baym et al. |
| 2017/0360313 | A1 | 12/2017 | Baek et al. |
| 2018/0078155 | A1 | 3/2018 | Baek et al. |
| 2018/0110667 | A1 | 4/2018 | Freeman et al. |
| 2018/0199834 | A1* | 7/2018 | Siedenburg .............. A61B 8/04 |
| 2018/0224534 | A1 | 8/2018 | Schulte |
| 2018/0235567 | A1 | 8/2018 | Bezemer et al. |
| 2018/0369065 | A1* | 12/2018 | Siedenburg .......... A61B 5/0205 |
| 2019/0053779 | A1* | 2/2019 | Siedenburg ........ A61B 5/02225 |
| 2019/0125191 | A1* | 5/2019 | Siedenburg ............ A61B 5/022 |

FOREIGN PATENT DOCUMENTS

| | | |
|---|---|---|
| WO | WO2016081517 A2 | 5/2016 |
| WO | WO2017032648 A1 | 3/2017 |

OTHER PUBLICATIONS

Murgo et al., "Aortic input impedance in normal man: relationship to pressure wave forms", Circulation. 62 (1): 105-16. doi:10.1161/01.CIR.62.1.105.PMID 7379273, Jul. 1980.

Rajan et al., "Review of methodological developments in laser Doppler flowmetry". Lasers Med Sci, 24:269-283, 2009.

U.S. Appl. No. 16/103,797, filed Aug. 14, 2018, titled "Constitutive equation for non-invasive blood pressure measurement systems and methods".

U.S. Appl. No. 15/999,038, filed Aug. 16, 2018, titled "Non-invasive blood pressure measurement devices, systems and methods".

Bercoff, et al., "Supersonic Shear Imaging: A New Technique for Soft Tissue Elasticity Mapping," IEEE Transactions an Ultrasonics, Ferroelectrics, and Frequency Control, vol. 51, No. 4, Apr. 2004, pp. 396-409.

Bernal, et al., "Material Property Estimation for Tubes and Arteries Using Ultrasound Radiation Force and Analysis of Propagating Modes," Journal of the Acoustical Society of America, vol. 129(3), Mar. 2011, pp. 1344-1354.

Beulen et al. "Toward Noninvasive Blood Pressure Assessment in Arteries by Using Ultrasound", Ultrasound in Med. & Biol., vol. 37, No. 5, May 2011, pp. 788-797.

The European Office Action dated Jan. 12, 2021 for European Patent Application No. 18703419.4, a counterpart foreign application of U.S. Appl. No. 15/874,796, 5 pages.

Hoeks, et al., "Non-Invasive Measurement of Mechanical Properties of Arteries in Health and Disease", Proceedings of the Institution of Mechanical Engineers, Part H: Journal of Engineering in Medicine, Mar. 1999, vol. 213 Part H, pp. 195-202.

International Search Report & Written Opinion, dated Jan. 25, 2018; International Application No. PCT/US2017/060708, filed Nov. 8, 2017; 9 pages.

International Search Report & Written Opinion, dated Apr. 17, 2018; International Application No. PCT/US2018/014273, filed Jan. 18, 2018; 14 pages.

Jensen, J., "Comparison of Vector Velocity Imaging Using Directional Beamforming and Transverse Oscillation for a Convex Array Transducer," SPIE Medical Imaging, San Diego, CA, Feb. 2014, p. 904012-1 to 904012-8.

Meinders, et al., "Simultaneous Assessment of Diameter and Pressure Waveforms in the Carotid Artery," Ultrasound in Medicine and Biology, vol. 30, No. 2, Feb. 2004, pp. 147-154.

Messas, et al., "Arterial Wall Elasticity: State of the Art and Future Prospects," Diagnostic and Interventional Imaging, Apr. 2013, pp. 561-569.

Montaldo, et al., "Ultrafast Compound Doppler Imaging: A New Approach of Doppler Flow Analysis," 2010 IEEE International Symposium on Biomedical Imaging: From Nano to Macro, Apr. 2010, pp. 324-327.

Office Action for U.S. Appl. No. 15/874,796, dated Jan. 28, 2021, Siedenburg, "Non-Invasive Blood Pressure Measurement Using Pulse Wave Velocity," 38 pages.

Office Action for U.S. Appl. No. 16/103,797, dated Apr. 28, 2021, Siedenburg, "Constitutive Equation for Non-Invasive Blood Pressure Measurement Systems and Methods", 16 pages.

Office Action for U.S. Appl. No. 15/874,796, dated Sep. 1, 2020, Siedenburg, "Non-Invasive Blood Pressure Measurement Using Pulse Wave Velocity," 39 pages.

Office Action for U.S. Appl. No. 16/103,797, dated Dec. 16, 2020, Siedenburg, "Constitutive Equation for Non-Invasive Blood Pressure Measurement Systems and Methods", 16 pages.

Office Action for U.S. Appl. No. 15/999,038, dated Mar. 25, 2021, Siedenburg, "Non-invasive blood pressure measurement devices, systems and methods", 27 pages.

Pereira et al., "Novel Methods for Pulse Wave Velocity Measurement", Physics Dept. Instrumentation Center, Univ. of Coimbra, Rua Larga, Coimbgra, Pt. J. Med Biol. Eng., Oct. 2015, 555-565.

Qi, et al., "Phase-Resolved Acoustic Radiation Force Optical Coherence Elastography," Journal of Biomedical Optics, vol. 17( 11), Nov. 2012, pp. 110505-1 to 110505-3.

(56) References Cited

OTHER PUBLICATIONS

Rabben, et al., "An Ultrasound-Based Method for Determining Pulse Wave Velocity in Superficial Arteries," Journal of Biomechanics, vol. 37, Oct. 2004, pp. 1615-1622.
Soleimani et al. "Assessing the Blood Pressure Waveform of the Carotid Artery Using an Ultrasound Image Processing Method" Univ of Tehran, IR, Ultrasonography, 36(2), Apr. 2017, pp. 144-152.
Struijk et al., "Blood Pressure Estimation in the Human Fetal Descending Aorta", Wiley InterScience, Ultrasound Obstet Gynecol, Oct. 2008, pp. 673-681.
Tijsseling, et al., "Johannes von Kries and the History of Water Hammer", Journal of Hydraulic Engineering-ASCE, vol. 133, Jan. 2007, 9 pages.
Rennin et al., "Noninvasive calculation of the aortic blood pressure waveform from the flow velocity waveform: a proof of concept", AM J Physiol Heart Circ Physiol 309: H969-H976, Jul. 2015.
Office Action for U.S. Appl. No. 15/999,038, dated Sep. 30, 2021, Siedenburg, "Non-Invasive Blood Pressure. Measurement Devices, Systems and Methods", 44 pages.

\* cited by examiner

LIGHT-BASED NON-INVASIVE BLOOD PRESSURE SYSTEMS AND METHODS

CROSS-REFERENCE TO RELATED APPLICATIONS

This patent application claims the benefit of and priority to U.S. Provisional Patent Application Ser. No. 62/577,982, filed on Oct. 27, 2017, entitled "LIGHT-BASED NON-INVASIVE BLOOD PRESSURE," the contents of which are hereby incorporated by reference in their entirety.

BACKGROUND

The blood pressure of a patient is a critical measurement that is used in monitoring and treating the patient. There are two means by which the blood pressure of the patient can be measured, one is invasive and the other is non-invasive. In the invasive means, the blood pressure is obtained by direct measurement, requiring a sensor to be inserted into the circulatory system of the patient to obtain the measurements. As such, the invasive means, while providing an accurate measurement, can cause discomfort in the patient or the subject for which the blood pressure is being measured. Additionally, there is an increased risk of complications and/or expense due to the invasive nature of such blood pressure measurement. Such increased complications risk and/or expenses can be unwarranted in many cases, such as during a simple patient examination.

In the non-invasive means, the sensing of the blood pressure is done externally to the patient. Typically, this involves the application of a cuff about a limb of the patient and the pressurization of the cuff to cut-off circulation through the limb. The pressure applied by the cuff to the limb is slowly reduced and as blood flow is resumed, the blood pressure can be measured based on the pressure remaining in the cuff. This process is often repeated multiple times to ensure an accurate measurement or as a means of monitoring over an extended period of time, with pauses required between measurement instances. While this means is non-invasive, it does require the temporary cessation of circulation in a portion of the patient, which can be damaging to the health of the patient and also requires time for the process to be fully performed. Additionally, such non-invasive blood pressure measurement techniques are sensitive to motion of the patient and/or equipment which can result in inaccurate and/or unobtainable blood pressure measurements. In patient transport or emergency situations, the patient and/or apparatus can be subjected to a large amount of motion during time in which an accurate blood pressure measurement can be critical to assess the state of the patient.

Blood pressure measurement and/or monitoring can be improved by non-invasive blood pressure systems and/or methods that do not require the restriction of circulation and provides the accurate blood pressure values/measurements needed for patient treatment and/or monitoring, including beat-to-beat blood pressure measurements that are conventionally the domain of invasive means.

DETAILED DESCRIPTION

Figure 1:
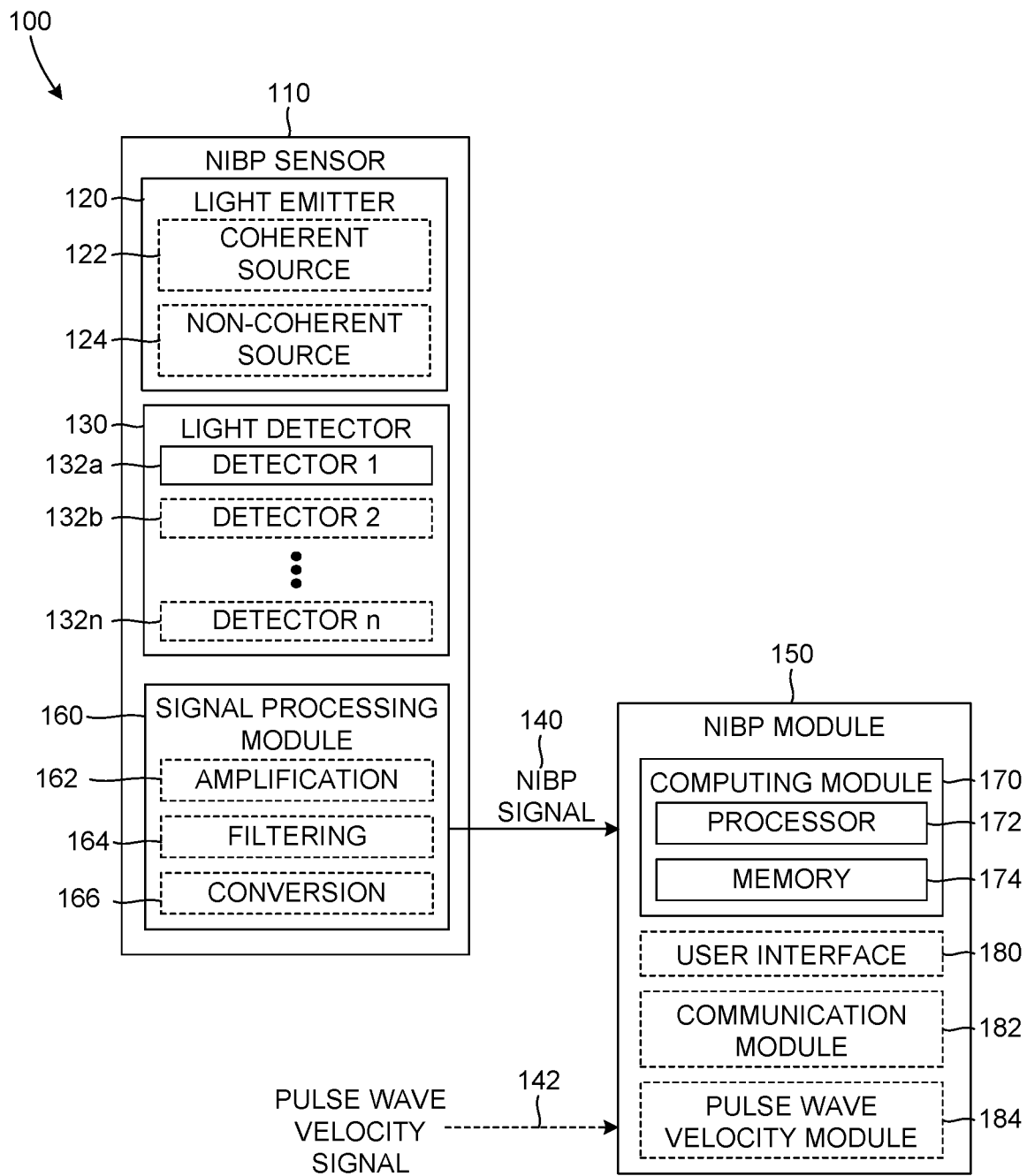
FIG. 1 is a block diagram of an example light-based non-invasive blood pressure system.

Embodiments of this disclosure measure two values that can be used to compute a patient's instantaneous blood pressure. Embodiments of this disclosure measure the instantaneous Non-Invasive Blood Pressure (NIBP) of a patient with an apparatus that determines the values for, in one example, two of the unknowns in the water hammer equation: pulse wave velocity (PWV) and instantaneous blood velocity ($v_i$). The water hammer equation relates instantaneous blood pressure to pulse wave velocity and blood flow velocity as follows:

$$P_i = \rho PWV\, v_i$$

where PWV is the pulse wave velocity, $\rho$ is the density of the blood that may be assumed to be a constant, for example, $v_i$ is the instantaneous velocity of the blood, and $P_i$ is the desired instantaneous blood pressure. Other equations relate instantaneous blood pressure to pulse wave velocity and blood flow, such as various constitutive equations, like those described in U.S. patent application Ser. No. 16/103,797, filed Aug. 14, 2018, titled "CONSTITUTIVE EQUATION FOR NON-INVASIVE BLOOD PRESSURE MEASUREMENT" and U.S. patent application Ser. No. 15/999,038, filed Aug. 16, 2018, titled "NON-INVASIVE BLOOD PRESSURE MEASUREMENT DEVICES, SYSTEMS, AND METHODS," which are incorporated by reference herein in their entirety. Those other equations relating instantaneous blood pressure to pulse wave velocity, blood flow velocity, and/or vessel mechanical characteristics or geometries may be used in determining the desired variables using the light-based emitters and detectors disclosed here.

Some conventional NIBP measurement systems rely on PWV to measure NIBP, but each requires an initial calibration measurement, taken at least once, to convert a relative blood pressure value to an actual blood pressure value. The required calibration measurement is taken using a traditional blood pressure cuff, for example on the arm or perhaps the finger. Such conventional NIBP measurement systems that require an initial calibration and all calculations are based on a difference or differential value of that initial calibration measurement and are therefore not an actual measurement of the blood pressure value.

The disclosed NIBP systems and devices instead take an instantaneous blood pressure measurement rather than a change from an initial calibration measurement. Avoiding the need for a calibration measurement prevents the patient from experiencing blood flow restriction altogether. Although PWV is highly correlated with blood pressure (BP) so that changes in blood pressure can be calculated from changes in PWV by relying on an initial calibration measurement relatively accurately, what has not been solved until now is how to eliminate the need to acquire and use a separate, initial calibration value or values to register a particular PWV to a particular value of blood pressure (as opposed to simply a change in blood pressure) for a patient. State of the art of NIBP using PWV typically uses a standard cuff-based measurement, to interrupt the blood flow, to measure and associate a particular blood pressure to a particular PWV measurement in a patient. Interrupting the blood flow requires that the patient's appendage being measured is compressed to restrict the blood flow. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary interruption of blood flow.

The lack of need for a calibration step for devices using the method taught herein arises from the use of the approximate relationships between $P_i$, $v_i$, and $A_i$, such as the water hammer equation in its integrated (non-differential) form. In the water hammer equation, the blood pressure is related to the PWV by a scale factor that can be known without a distinct calibration step. The scale factor can be found using the same ultrasound and/or light-based technology that is used to measure the PWV. That scale factor is related to the blood velocity and blood density. In this way, a particular blood pressure is calculated as the PWV scaled by the blood density and the blood velocity.

Blood velocity can be acquired using light and/or ultrasound as a time varying waveform. PWV can also be measured with light and/or ultrasound also as a time varying function. The time-varying nature of the PWV means that it can be updated from beat to beat if desired. The time-varying nature of the blood velocity means that blood velocity can be measured at a much finer resolution than a cardiac cycle, that is to say, continuously during the cardiac cycle for as many cardiac cycles as is desired. Because blood density is already sufficiently known and is relatively constant, not only can a particular blood pressure measurement be known as if it were obtained by a standard cuff-based measurement, but all manners of blood pressure measurements can be made as time-varying waveforms describing the instantaneous pressure at as many points during a cardiac cycle as desired. That is to say, blood pressure can be monitored continuously throughout the cardiac cycle with as fine a resolution as is required, and this can be done for as many contiguous cardiac cycles as is desired for beat-to-beat monitoring, or as intermittently as desired for long term monitoring.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. In the embodiments discussed below, light-based technology is used to acquire the blood velocity and/or the PWV although other methods of obtaining the PWV and/or the blood velocity can alternatively or additionally be used. Further embodiments implement various techniques and devices to measure or detect instantaneous blood velocity. As is described in greater detail below, specific embodiments simplify the task of measuring NIBP without sacrificing reliability. Still further, embodiments enable the measurement of (or at least an estimation of) NIBP without requiring calibration that relies on a separate means for detecting blood pressure, which simplifies the treatment and evaluation of the patient.

This disclosure begins with a description of one example of a medical device that may be used in specific embodiments. Next is a discussion of one embodiment of a sensor for measuring NIBP using ultrasound. Alternative embodiments for sensors which measure NIBP are further discussed.

FIG. 1 illustrates a non-invasive blood pressure (NIBP) measurement system 100 that includes an NIBP sensor 110 and an NIBP module 150. The NIBP sensor 110 is placed on and/or near a patient to generate and transmit an NIBP signal 140 to the NIBP module 150. The NIBP signal 140 is indicative of the blood velocity and vessel wall motion of the patient and is processed by the NIBP module 150 to determine/calculate the blood pressure of the patient. The NIBP measurement system 100, as shown in FIG. 1, allows for the efficient and accurate acquisition of the patient's blood pressure.

The NIBP sensor 110 includes a light emitter 120 and a light detector 130. Alternatively, the NIBP sensor 110 can include multiple light emitters 120 and/or light detectors 130. The NIBP sensor 110 is placed on and/or near a patient, such as against the skin of the patient, so that the light emitter 120 and the light detector 130 are in contact with or proximally located to the patient. The light emitter 120 emits light that is transmitted into the tissue of the patient and reflected from various tissues, such as blood vessels, various fluids, such as blood, and/or other features of the patient's anatomy. The reflected light is detected by the light detector 130, which outputs the NIBP signal 140 indicative of the motion of and within the patient's vasculature, the various tissues, fluids and/or other features of the patient's anatomy.

The light emitter 120 can include a coherent light source 122 and/or a non-coherent light source 124. The coherent light source 122 emits coherent light which are light waves that are of one phase and frequency. An example coherent light source 122 is a laser. The coherent light source 122 can also be a light source that emits non-coherent light that is then filtered, processed and/or manipulated so that the light transmitted into the tissues of the patient is coherent. A non-coherent light source 124 can be a light source that emits light in one or more phases and/or having one or more frequencies and/or waveforms. Example non-coherent light sources can include light emitting diodes (LEDs), incandescent, fluorescent, halogen and other non-coherent light emitting sources.

In an example embodiment, an example non-coherent light source 124 can include a narrow or wide bandwidth non-coherent light source. That is, the non-coherent light source 124 can emit light having a relatively narrow range of variability, or a relatively small or narrow bandwidth. For example, a narrow bandwidth, non-coherent light source can include an LED that emits light across a relatively small range of frequencies. A non-coherent light source, such as an LED, can be used for one or more optical interferometry techniques, such as low-coherence interferometry, to acquire and/or determine an instantaneous blood velocity of the patient.

The light emitted by one or both of a coherent light source 122 and a non-coherent light source 124 can be in a visible, non-visible, or mixed spectrum of light emission. That is, the light emitted by the light emitter 120 can be within a spectrum of light visible to the human eye, can be in a light spectrum non-visible to the human eye, or a mix of light including light in both the visible and non-visible spectrum. Example visible light can include colored light, such as visible light having a longer wavelength within the red portion of the visible spectrum and/or a visible light having a shorter wavelength within the blue/violet portion of the visible spectrum. Non-visible light can include short wavelength non-visible light, such as ultraviolet light, and long wavelength non-visible light, such as infrared light.

The one or more light sources 122 and/or 124 of the one or more light emitters 120 can be selected based on the properties, such as wavelength, frequency, intensity and/or other properties of the light emitted from the light source 122 and/or 124. In an example embodiment, the light source 122 and/or 124 can be selected based on the wavelength of light emitted from the light source 122 and/or 124. In human tissues, some wavelengths of light have greater penetrating capabilities, such as some infrared wavelengths, for example, indicating that the light emitted by the light source 122 and/or 124 travels further into the tissues of the patient before being absorbed and/or reflected. The increased penetration depth of some longer wavelength light can increase the tissue depth in which the NIBP system 100 can accurately determine the blood pressure of the patient and/or other patient physiological properties, such as blood vessel geometry and/or dynamics.

The light emitter(s) 120 and/or the light sources 122, 124 can be oriented and/or include a directional element to direct the light towards the tissues of a patient. In this manner, the emitted light can be controlled and/or directed along a selected and/or desired pathway. For example, the emitted light can be directed to enter the patient tissues at a specified angle, and/or range of angles, of incidence with respect to the flowing blood through the vessel. After interacting with the vessel wall, proximate tissue, and/or flowing blood, reflected/scattered light either reverses direction back towards the same side the light entered at a second angle back towards the detector (reverse scatter) or continues to the detector on the opposite side of the interrogated vessel (forward scatter). The type of scatter is dependent on the position of the detector relative to the emitter.

In an example embodiment, a directional element, such as a diffuser and/or lens can be used in conjunction with the light emitter(s) 120. One or more diffusers can be located between the light emitter(s) 120 and the patient to diffuse the emitted light from the light emitter(s) 120. Diffusing the light emitted from the light emitter(s) 120 can increase the area illuminated by the light, such as the area through which the emitted light is transmitted into and/or through the tissues of the patient. In the example of a coherent 122 and/or a non-coherent light source, the light emitted by such sources is typically focused to a relatively narrow or small cross-sectional area. Diffusing the emitted coherent, or non-coherent, light increases the cross-sectional area of the emitted light which increases the cross-sectional area of the patient tissues illuminated by the emitted light. The wider area of the diffused light can increase the likelihood of the emitted light contacting and reflecting off of a blood vessel and/or blood therein. Non-diffused light illuminates a smaller cross-section of the patient tissues which can require movement of the NIBP sensor 110 to properly position the NIBP sensor 110 so that the light from the light emitter(s) 120 interacts with a blood vessel of the patient in order to allow for the determination, capture and/or calculation of the instantaneous blood velocity of the patient.

Additionally, two or more of the light emitter(s) 120 and/or the light sources 122, 124 can emit light have varying and/or different properties. That is, the NIBP sensor 110 can simultaneously and/or sequentially emit light having varying properties, such as varying intensities, frequencies, wavelengths and/or other light properties. Emitting light having varying and/or different properties can create multiple NIBP signals that can be processed by the NIBP module 150 to determine a blood pressure of the patient in a non-invasive manner. The use of multiple and/or different light emitter(s) 120 and/or light sources 122, 124 may assist with error reduction and increasing accuracy of the determined/calculated blood pressure using the light-based NIBP system 100.

In an embodiment, an example NIBP sensor can include both a coherent source 122 and a non-coherent source 124. Light from one or more of the sources 122, 124 can be selectively emitted in a continuous and/or intermittent manner, such as first emitting light from the coherent source 122 and second from the non-coherent source 124. The two sources 122, 124 can be individually disposed on the NIBP sensor 110 in separate light emitters 120, or can be integrated into a single light emitter 120. A dedicated reference path exists between the non-coherent source 124 and on or more light detectors 132a-132n of the light detector 130. Alternatively, each source 122, 124 can be paired with an individual light detector 130.

The NIBP sensor 110 also includes one or more light detectors 130 that can include one or more detectors 132a, 132b . . . 132n, to detect light, emitted from the one or more light emitters 120, that is reflected from tissues, blood and/or other components of the patient. The light detector(s) 130 can detect one or more properties of the incoming light to generate a signal, such as an NIBP signal (e.g. motion signal from blood flow or vasculature walls) 140, that can be output from the NIBP sensor 110 to the NIBP module 150 for processing. Example properties of the incoming light that can be detected by the light detector(s) 130 can include the frequency, phase change, wavelength, intensity and/or other properties of the incoming light. The NIBP signal 140 output from the NIBP sensor 110 to the NIBP module 150 is indicative of the detected property(s) of the light detected by the light detector(s) 130.

One or more light detectors 130 and/or one or more detectors 132a, 132b . . . 132n can be distributed and/or arranged on the NIBP sensor 110 to detect light reflected from various tissues, fluids and/or other features of the patient's anatomy. Each of the light detectors 130 and/or the detectors 132a, 132b . . . 132n can be associated with one or more light emitters 120 and/or sources 122, 124. Alternatively, a single light detector 130, and/or detector 132a, can be included to detect the reflected light from the patient tissues and/or fluids.

The light detector 130 and/or the detectors 132a, 132b . . . 132n, can be arranged relative to and/or spaced from the light emitter(s) 120 and/or light sources 122, 124.

The spacing between the emitter and the detector influences and/or determines the tissue depth from which reflected light can be detected especially with incoherent or broad band sources. The reflected light waveform arrives at the detector along a reference path (having no significant motion) along with that which is reflected from the patient tissues. The light detector(s) 130, and/or the detectors 132a, 132b . . . 132n, are positioned and/or sized to detect the reflected light based on the depth of the tissue from which the light is reflected. For coherent light, for example, the correlation is periodic so that there is little depth discrimination. For incoherent light, the depth is highly resolved as the path length between the light emitter and the light detector along the reference path is the same as the path length through the tissue because the light waveform has a very small correlation length.

The arrangement of the light emitter(s) 120 and/or light sources 122, 124 relative to the light detector(s) 130 and/or detectors 132a, 132b . . . 132n can be used to determine depth information based on the detected reflected light. As the spacing between the emitted light and the detected light is known based on the arrangement of the emitter and detector, or components thereof, the depth of the tissue off which the emitted light reflected could be determined, particularly for incoherent source 124. The depth information can be informative of the depth of certain tissue types, such as a blood vessel, and can also be used to determine the size of tissue features, such as the cross-sectional area and/or wall thickness of a blood vessel.

In an example embodiment, the light detector 130 can include an array of detectors 132a, 132b . . . 132n that are arranged in a grid formation. Each of the detectors 132a, 132b . . . 132n can generate a signal that includes information regarding the positioning of the detector 132a, 132b . . . 132n within the grid formation. In this manner, the NIBP signal 140 generated by each detector 132a, 132b . . . 132n includes properties of the detected light and spacing information to determine a depth from which the light was reflected based on the spacing between the detector 132a, 132b . . . 132n and light emitter 120.

The NIBP sensor 110 can be a self-contained device or included as a part of another device. For example, both the NIBP sensor 110 and the NIBP module 150 can be included in a single device. Alternatively, the NIBP sensor 110 can be fully or partially self-contained and can transmit the NIBP signal 140 to a separate NIBP module 150, such as via a wired or wireless connection. In a fully self-contained example, the NIBP sensor 110 can include the necessary hardware to output the NIBP signal 140, such as including a power source for providing the necessary energy to the light emitter(s) 120 and/or transmit the NIBP signal 140 to the NIBP module 150, such as via a wired or wireless connection. In a partially self-contained example, the NIBP sensor 110 can include all or a portion of the hardware required to generate and transmit the NIBP signal 140 and require input and/or the assistance of another connected device to generate and/or transmit the NIBP signal 140, such as requiring a connection to a power source. Such a power source can be included in the NIBP module 150, with a wired or wireless connection between the NIBP sensor 110 and the NIBP module 150 allowing for the transfer of data, such as the NIBP signal 140, and power from a power source of the NIBP module 150 or an external power source coupled thereto.

The NIBP sensor 110 can be constructed to allow it to be reusable on many patients. As part of the reusability, the construction of the NIBP sensor 110 allows the NIBP sensor 110 to be disinfected, cleaned, sterilized or otherwise receive the requisite cleaning necessary for use on multiple patients. The various components, such as the light emitter(s) 120 and/or the light detector(s) 130 can be protected by a cleanable covering that does not distort and/or adversely affect the emission and/or detection of the light through the cleanable covering. In an embodiment, the covering is a film based covering that can be removed and replaced to maintain a requisite cleanliness or the film can be a layer of individual films that can be removed individually between uses of the NIBP sensor 110 or the covering could be the diffuser/lens.

In another embodiment, the NIBP sensor 110 can be a disposable article, such as a patch, that can be applied to the patient to acquire, process and/or transmit the NIBP signal 140. Both the light emitter(s) 120 and the light detector(s) 130 can be disposed on the patch and the patch can be powered by a connection to the NIBP module 150 which can also supply power to the patch. The transmission of power and/or data can be through a wired connection, such as by a cable, and/or a wireless connection, such as by inductive power coupling and/or wireless data transmission or energy harvesting technology or by a local battery.

During use, the NIBP sensor 110 is placed on or against a patient to allow the light emitter(s) 120 to transmit light into the patient's tissues and for the light detector(s) 130 to detect the light reflected therefrom. The NIBP sensor 110 structure can include a handle or other features to assist a user with placing and/or restraining the NIBP sensor 110 against the tissues of the patient.

To assist with an extended monitoring of a patient's blood pressure using the NIBP system 100, the NIBP sensor 110 can be affixed or secured to the patient during the extended monitoring period. During the monitoring period, the NIBP system 100 can acquire the blood pressure of the patient selectively and/or regularly. The acquisition of the blood pressure of the patient can be automatically initiated/triggered, such as by a predetermined schedule, a triggering event/physiological measurement and/or by a signal from an external device/system. Additionally, or alternatively, the acquisition of the blood pressure of the patient can be manually triggered, such as by a user actuation of the NIBP system 100 and/or by a user caused signal from an external device/system. The NIBP sensor 110 can include positioning elements to assist with minimizing motion of the NIBP sensor 110 when placed on a patient. For example, the NIBP sensor 110 can include a cuff, or other garment or restraint, to constrain the NIBP sensor 110 in a relative position on the patient. The band or restraint can be selectively releasable to ease the securement and removal of the NIBP sensor 110 from the patient. Alternatively, the NIBP sensor 110 can be adhered to a patient, such as with a temporary adhesive. The NIBP sensor 110 itself can have the adhesive pre-applied or the adhesive can be applied by a user to the NIBP sensor 110 or the patient in preparation for affixing the NIBP sensor 110 to the patient. Additionally, other suitable securing means, such as surgical tape and/or elastic bandages, can be used to secure the NIBP sensor 110 to the patient.

The NIBP system 100 also includes a signal processing module 160, a computing module 170, an optional display 180, an optional communication module 182 and a pulse wave velocity (PWV) module 184. The NIBP module 150 can be a separate device from the NIBP sensor 110 or the NIBP module 150 and the NIBP sensor 110 can be integrated in, or as a portion of, a single device, such as another patient monitoring and/or treatment device(s). The NIBP module 150 and the NIBP sensor 110 can be communicatively coupled to assist with transmitting the NIBP signal 140 from the NIBP sensor 110 to the NIBP module 150.

The NIBP module 150 receives the NIBP signal 140 for processing and use in determining/calculating the blood pressure of the patient. The NIBP signal 140 includes a Doppler signal caused by the reflection of the emitted light off moving components of the patient's tissues when compared to an intrinsic or extrinsic reference path, namely the flowing red blood cells within a vessel. The light emitted by the light emitter(s) 120 penetrates or passes through the patient's tissues and reflects from various components thereof, including blood as it flows through a vessel. The light reflected from the moving blood experiences a frequency shift from the emitted light due to the reflection of the light from a moving surface of one or more blood cells. The frequency, or Doppler, shift can be processed to determine the instantaneous velocity ($v_i$), or speed, of the moving blood through the vessel. The combination of the calculated/determined instantaneous velocity of the patient's blood, the PWV of the patient and the essentially universal density of blood ($\rho$) can be used to calculate the instantaneous blood pressure ($P_i$) of the patient, such as through the use of Equation 1, for example:

$$P_i = \rho PWV v_i \qquad \text{(Equation 1)}$$

The signal processing module 160 processes the raw data to produce the NIBP signal 140. As part of the signal processing, the signal processing module 160 can include amplification 162, filtering 164 and/or conversion 166 of the received signal. The various signal processing procedures, such as amplification 162, filtering 164 and/or analog-to-digital conversion 166, can prepare the NIBP signal 140 for processing to determine and/or calculate the instantaneous blood velocity ($v_i$) of the patient as well as optionally determining and/or calculating PWV in some examples.

Amplification 162 of the NIBP signal 140 can be performed using a low-noise amplification (LNA) element and/or circuit to amplify the NIBP signal 140 while minimizing the degradation of the signal-to-noise ratio of the original NIBP signal 140. Amplification 162 can be necessary for processing the NIBP signal 140, as the NIBP signal 140 generated by the NIBP sensor 110 can be a low power signal in this example. The amplified NIBP signal 140 can then be filtered 164, such as by the use of an anti-alias filtering element and/or circuit, in preparation for conversion 166. The conversion 166 of the amplified and filtered NIBP signal 140 can convert the analog signal to a digital signal using an analog-to-digital conversion element and/or circuit. Upon completion of the signal processing of the NIBP signal, the NIBP signal 140 can then be processed to determine and/or calculate the instantaneous velocity of the patient's blood as well as optionally determining and/or calculating PWV using start-of-the-art means. In a further embodiment, all or a portion of the signal processing of the NIBP signal 140 can be performed at the NIBP sensor 110 prior to transmission of the NIBP signal 140 to the NIBP module 150. Alternatively, the NIBP signal can be processed without the use of one or more of the intervening signal processing steps.

The NIBP signal 140 is processed or directed, depending on the NIBP system 100 configuration, to be analyzed/evaluated by the computing module 170 to determine/calculate the instantaneous blood velocity. The analysis/evaluation of the NIBP signal 140 can include further processing, such as additional filtering, such as by a high-pass, low-pass, and/or band-pass filtering element and/or circuit, to isolate the relevant portion of the NIBP signal for analysis/evaluation. Additionally, the NIBP signal can be decimated if the bandwidth of the signal is sufficiently low. The Doppler data of the NIBP signal can then be scaled to determine the instantaneous blood velocity and/or analyzed for additional data about the vasculature of the patient, such as the cross-sectional diameter of the vessel as a function of time. Additionally, the Doppler spectrum of the data can be scaled in frequency based on the angle of incidence of the emitted light relative to the patient tissues/blood flow of interest as well as the angle relative to the same tissue/blood flow as it reflects to arrive at the detector. The values of the angles described can be entered by a user, assumed value(s) and/or determined based on vasculature information including the orientation of the vessel.

Alternatively, one or more of the determined/calculated value of the instantaneous blood velocity and/or one or more vessel dynamics, such as the cross-sectional diameter, for example, can be transmitted to the computing module 170 to determine/calculate the instantaneous blood pressure of the patient.

The computing module 170 includes a processor 172 and memory 174. The processor 172 can execute various functions and/or programming, such as that stored in the memory 174 or other storage locations. The various functions can include controlling one or more operations of the NIBP module 150 and/or the NIBP sensor 110, such as the determination/calculation of an instantaneous blood pressure based on the instantaneous blood velocity and PWV of a patient. In an embodiment, one or more functions of one or more components of the NIBP system 100 can be integrated with the computing module 170, or vice versa. For example, one or more components, functions and/or capabilities, or portion thereof, of the signal processing module 160 can be integrated with and/or performed by the computing module 170, or vice versa. Additionally, one of more functions and/or capabilities, or portion thereof, of the communication module 182 can be integrated with the computing module 170. Further, the computing module 170 can include and/or be connected to an interface, device and/or system for receiving input from one or more of a user, a device and/or a system remote from the NIBP module 150 and/or the NIBP system 100.

The computing module 170 can calculate the instantaneous blood velocity and/or one or more vessel dynamics based on the NIBP signal 140 and can receive a pulse wave velocity of the patient, such as from the pulse wave velocity module 184. Using these two values and an assumption of a relatively universal blood density, the instantaneous blood pressure of the patient can be determined/calculated, such as by using Equation 1 above. The instantaneous blood pressure can then be output to a display and/or communicated to another device and/or system for display and/or use in one or more device/system functions.

The computing module 170 can also process and/or use the received information, such as the NIBP signal 140, the PWV and/or other information received by, detected by and/or input to the computing module 170 to determine, calculate and/or otherwise process the various available information to assess one or more vascular, hemodynamic, and/or physiological parameters. For example, the computing module 170 and/or the NIBP module 150 can process various information, including the NIBP signal, to measure one or more vascular parameters, such as the cross-sectional diameter of a vessel, and one or more cardiac performance parameters. These measurements and/or other measurements/assessments based on the information that is able to be processed by the computing module 170 and/or the NIBP module 150 can provide insight into the physiological performance and/or parameters of a patient monitored by the NIBP system 100. Additionally, the information calculated and/or determined by the NIBP system 100 can be communicated, such as via the communication module 182, to one or more devices, systems and/or users remote from the NIBP system 100. This communicated information can be used by one or more of the remote devices, systems and/or users for various other processes, such as patient treatment, patient data collection, patient monitoring, post-event reviews/audits, statistical data collection and/or other processes/uses.

The NIBP module 150 can include an optional display 180 that can display, or show, information to a user. In an example, the display 180 can include indications to a user regarding the NIBP system 100, such as the detection, or lack thereof, of a blood vessel, an indicated depth of a detected blood vessel, an instantaneous blood velocity, a pulse wave velocity and/or a blood pressure value. Alternatively, or additionally, the display 180 can include information regarding the patient, such as an identification, and/or information regarding the NIBP system 100, such as a status of the system 100 and/or one or more components of the system 100. Status information of the NIBP system 100 can include maintenance and/or use related information, such as an indication that the NIBP system 100 requires maintenance or instructions to prompt the user to reposition the NIBP sensor 110 if the NIBP sensor 110 is currently not detecting a blood vessel.

The display 180 can include display formats that display actual values regarding the displayed information or can display qualities of the displayed information. For example, the display 180 can display an actual value of a measured variable and/or the display 180 can display an indication of the value, such as indicating a position of the value on a scale indicating one or more ranges associated with qualifiers such as an acceptable or unacceptable status. The formats of the display 180 can include digital formats that alter the display to show information or can include analog formats that indicate the information on a scale or other format. In an example, the display and/or an audio element, such as a speaker, can provide a notification/alerts if a value, such as a blood pressure, deviates from a normal value and/or range. This alert/notification can inform a user, or others, to the abnormal measured and/or determined value of the patient physiological parameter, such as the patient's blood pressure.

In addition to being an output device, the user interface 180 can be and/or can include an input/output means for a user to input information into the NIBP module 150 and/or NIBP system 100. For example, the user interface 180 can include a touchscreen capability to allow the user to interact with and/or control the NIBP module 150 and/or NIBP system 100. The NIBP module 150 and/or NIBP system 100 can query the user for input, such as for inputting settings and/or other information, and can receive the requested information via a user input using the input capabilities of the display 180. Example user input can include a selection of a light source 122, 124 to use and/or other selection(s) of controllable aspects of the NIBP system 100.

The communication module 182 can provide a communication pathway between the NIBP module 150 and/or the NIBP system 100 via one or more wired and/or wireless connections. Various communication protocols and/or pathways can be supported by the communication module 182 to allow the NIBP module 150 and/or NIBP system 100 to communicate with remote devices, systems and/or users. For example, the communication module 182 can facilitate communication between the NIBP module 150 and/or the NIBP system 100 with one or more remote devices, systems and/or users through a local network and/or internet based connection, such as a Wi-Fi, Bluetooth®, WiGig, and/or other connection/communication protocol, method and/or standard. Communications from the communication module 182 can optionally be encrypted and/or transmitted across a secure communication link established between the communication module 182 and an external device/system. The secure communications can prevent the dissemination of confidential patient information and also can protect the integrity of the communication from outside influence and/or manipulation, especially during software upgrades.

The communication module, or other component/system of the NIBP module 150, can include user validation functionality. The user validation functionality can limit the available features/functionality of the NIBP system 100 and/or provide instruction based on the user and their credentials/validation. For example, a doctor, nurse or healthcare worker can be validated by the user validation functionality as a trained user of the NIBP system. In response, the communication module 182 can communicate the user level/validation to the computing module 170 to allow, unlock and/or expand one or more functions/features of the NIBP system 100. In another example, the user can be an untrained individual and the user validation functionality can validate as such. In response, the communication module 182 can communicate the user level/validation to the computing module 170 to restrict one or more functions/features of the NIBP system 100. Additionally, the NIBP system 100 can provide instructions based on the user level/validation, such as providing additional instructions to users validated as having a lower training/experience level. User credentials/validations can be transmitted/communicated to the communication module 182 via a physical user input, such as via a numerical keypad and/or touchscreen, or via a wireless input, such as contactless identification card, such as near field communication (NFC), and/or other wireless data transmission device/system. The user validation functionality can also include optional confirmation of the user credentials/validations by confirming the received user credentials/validations with a remote device/system, such as a server, via the communication module 182.

In addition to communication with a remote device, system and/or user, the communication module 182 can support communication between the NIBP module 150 and one or more NIBP sensors 110. Communication between the NIBP module 150 and one or more NIBP sensors 110 can be via a wired and/or a wireless connection. The connection can support the transmission of data, such as the NIBP signal, from the NIBP sensor 110 to the NIBP module 150 and/or the transmission of data, such as commands to control the light emitter(s) 120, from the NIBP module 150 to the NIBP sensor 110. That is, the connection between the NIBP sensor 110 and the NIBP module 150 can be a two-way connection to allow the transmission of data, commands and/or other communication between the NIBP sensor 110 and the NIBP module 150.

Additionally, the communication module 182 can be modular and/or expandable to allow upgrading and/or replacement of one or more communication modules 182. For example, the communication module 182 can facilitate secured communications between the NIBP module 150 and/or the NIBP system 100. The secure communication network/protocol can require specific hardware to allow the NIBP module 150 and/or NIBP system 100 to access the secure communication network/protocol. To allow the NIBP module 150 and/or NIBP system 100 to access the secure communication network, the proper communication module 182 can be inserted into and/or otherwise coupled to the NIBP module 150 and/or NIBP system 100.

The NIBP module 150 can include an optional pulse wave velocity module 184 that can determine a pulse wave velocity of a patient, receive information related to the pulse wave velocity of the patient and/or connect to one or more devices to capture the data for use in determining a pulse wave velocity of the patient. Pulse wave velocity (PWV) is the velocity at which the pressure wave, caused by arterial pulse, propagates through the circulatory system of a patient, or other. Pulse wave velocity information can be sensed by the NIBP system 100 and/or another device/system near, or substantially, simultaneously as the collection of the NIBP signal 140. This near, or substantially, simultaneously acquisition of PWV data and blood velocity data negates the need for a calibration step to determine an accurate blood pressure using Equation 1, for example. Equation 1 is representative of a solution to one of several possible mathematical partial differential equations describing the physics relating blood pressure, blood velocity, and vessel area and diameter. The disclosure can rely on any of the mathematical equations that relate blood pressure, blood velocity, and vessel area and diameter (vessel geometries), such as one or more constitutive equations described in U.S. patent application Ser. No. 16/103,797, filed Aug. 14, 2018 entitled "CONSTITUTIVE EQUATION FOR NON-INVASIVE BLOOD PRESSURE MEASUREMENT SYSTEMS AND METHODS," which is incorporated by reference herein in its entirety.

The pulse wave velocity received and/or determined by the pulse wave velocity module 184 and the instantaneous blood velocity information determined by the NIBP system 100, can be used, such as by Equation 1, to determine the instantaneous blood pressure of a patient. PWV data can be collected using the NIBP system 100, such as through processing the NIBP signal 140, and/or can be received from an external device/system as a pulse wave velocity signal 142. The pulse wave velocity signal 142 can be obtained using various techniques, such as pulse wave Doppler (PWD) and/or continuous wave Doppler (CWD) techniques to obtain raw signal data that is processed to determine and/or calculate the PWV. Ultrasound and/or light-based systems and/or device can use the techniques, such as PWD and/or CWD, to collect PWV data for use by the NIBP system 100. Additionally, the PWV and/or the instantaneous blood velocity measurements and/or vessel geometry can be used to determine additional circulatory data, such as vessel information, cardiac output and/or other measurements or circulatory performance metrics.

Figure 2:
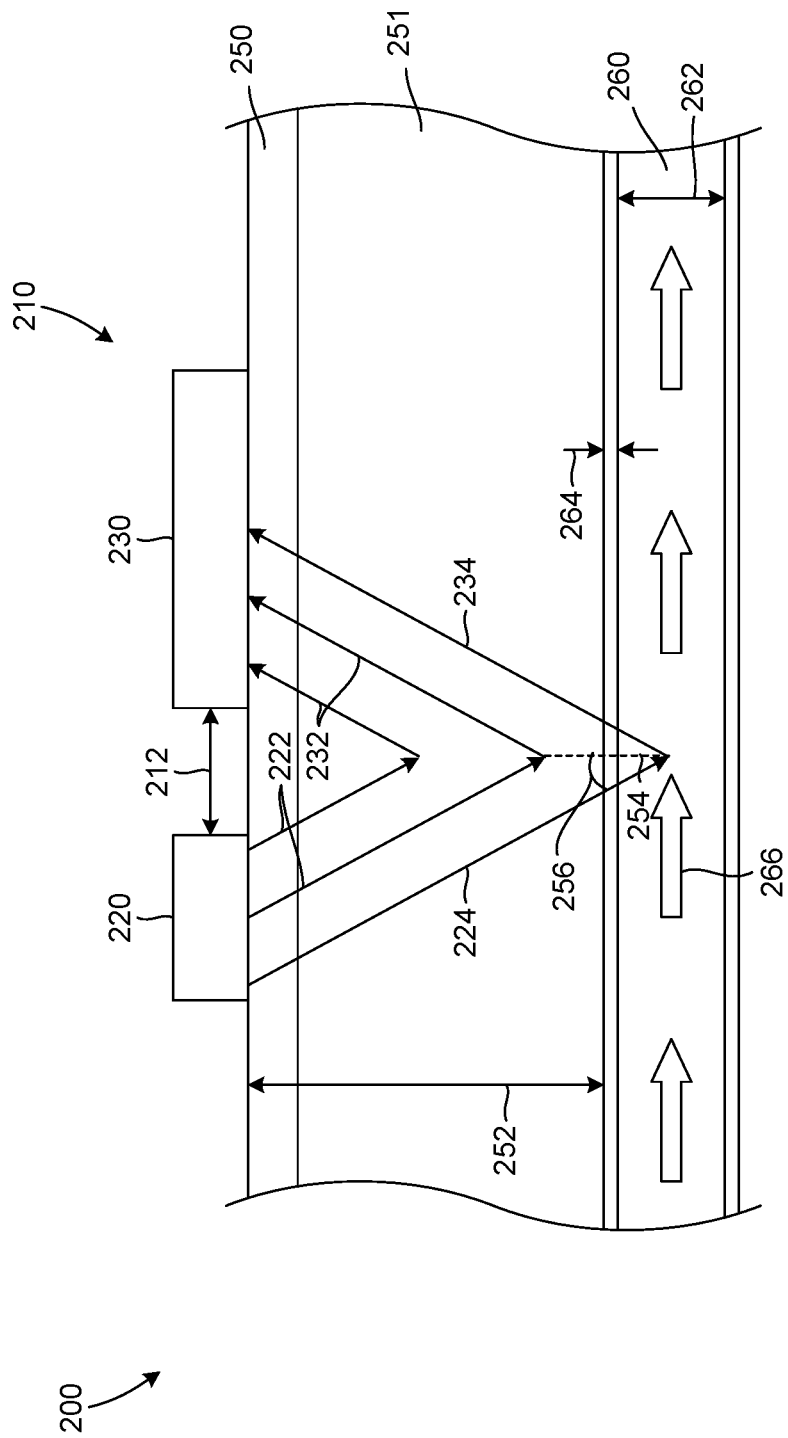
FIG. 2 is an example light-based non-invasive blood pressure system with a coherent light source.

FIG. 2 illustrates an example light-based non-invasive blood pressure system 200 with a coherent light source. An NIBP sensor 210 is shown, including a light emitter 220, with a coherent light source and a light detector 230. The light emitter emits light 222 and 224 through skin 250 into deeper tissue 251 containing blood vessel 260. The light detector 230 receives reflected light 232 and 234 that is reflected from tissue 251 and blood vessel 260. The skin 250 and tissue 251 has a depth 252, or thickness, to the blood vessel 260, which has a vessel diameter 262, a vessel wall thickness 264 and a blood flow 266. The reflected light 232, 234 from the various tissues/features of the tissue 251 and blood vessel 260 is received by the light detector 230 to generate an NIBP signal that can be processed to determine measurements of the tissues/features, such as an instantaneous blood velocity, which can be used in various calculations to determine one or more physiological parameters, such as an instantaneous blood pressure.

In the example shown in FIG. 2, the light emitter 220 includes a coherent light source, such as a laser diode that emits the light 222, 224. The coherent light source emits light at a fixed frequency that is sufficiently low to penetrate the tissue 251 and/or vessel 260, such as infrared light. Other coherent light sources capable of emitting light that sufficiently penetrates tissues, such as skin 250 and vessel 260, can be used. The maximum depth of penetration of the emitted light, such as 222, 224, is determined at least in part by the spacing distance 212 between the light emitter 220, or light source contained therein, and the light detector 230, or the light detector therein. Additionally, a relative absorption of the path lengths of the emitted light, such as 222, 224, the directivity of the light source of the light emitter 220 and/or an angle supporting the greatest reflection of light, at least in part, influence the maximum depth that the emitted light 222, 224 can penetrate into the tissue 251, 260.

As the emitted light 222, 224 is transmitted into and through the tissues 251, 260, a portion of the emitted light is absorbed by the tissues 251, 260. This absorption reduces the energy of the light transmitting through the tissues 251, 260 so the relative absorption of the light along the path lengths of the light emitted, such as 222, 224 influences the energy of the reflected light 232, 234 reflected from the tissues 251, 260. The energy of the reflected light 232, 234 needs to be sufficient to reach the light detector 230 and/or be detectable by the light detector 230 to generate an NIBP signal. Therefore, the relative absorption of each of the path lengths of the emitted light 222, 224 has an effect on the maximum depth to which the emitted light 222, 224 can be transmitted to sufficiently reflect as reflected light 232, 234 and be detectable by the light detector 230.

The angle of the emitted light, such as 222, 224, relative to the tissues 251, 260 supporting the greatest reflection of light received at the detector 230 is the "angle of incidence" of the emitted light. The angle(s) of incidence, among other Doppler contributors, from the tissues 251, 260, results in the reflected light 232, 234 with the greatest energy and/or is the angle at which the incidence angle of the light relative to and contacting the tissues 251, 260 is substantially similar to the reflection angle of the light relative to and reflecting from the tissues 251, 260 on its way to the detector 230. These two angles each cause a change in frequency in the signal as perceived by the detector 230 (between the light emitter and the flowing blood and the flowing blood and the detector, respectively) and together can be used to calculate the Doppler correction factor.

An angle 256 is the incidence angle of the emitted light 222, 224 relative to a normal 254 of the interrogated tissue 251. The angle 256 can be based on an orientation of the light source of the light emitter 220, such as positioning/orienting the light source to project/emit light, and/or directing the emitted light, so that it reflects from the tissue at an angle relative to the normal 254 as the light is transmitted towards the flowing blood. The angle 256 can be also be based on the refraction of the emitted light, such as 222, 224, caused by the difference in propagating characteristics between the material covering the source 220 and the tissue it is in contact with, for example, the index of refraction of 251, 260. The range of angles of light emitted from the light source can also have an effect on the angle 256 of the emitted light entering the tissues 251, 260 from the light emitter 220 and/or the light source therein.

To determine an instantaneous velocity of the blood flow 266 in the vessel 260, light 224, emitted from the light emitter 220, is transmitted through the tissues 251, 260 to contact the blood flow 266 and reflect therefrom, as reflected or scattered light 234. The reflected light 234 is received by the light detector 230 and has a Doppler frequency, or shift, from the emitted light 224, due to the reflection of the light 234 from a moving fluid, or component thereof, which is the flowing blood 266. In addition to receiving the Doppler shifted reflected light 234, the light detector 230 also receives light 232 that is reflected from non-moving tissues, such as skin and tissue between the skin and the exterior vessel wall on either or both sides of the vessel. The reflected light 232 and 234 are received by the light detector 230, and cause a signal to be generated in response to and based on the detected light 232, 234.

The low frequency AC portion of the reflected light signal, caused by photodetection of the light 232 and 234 by the light detector 230, is the difference frequency/Doppler portion of the signal. The DC portion is the sum of incident power of the Doppler shifted signal, caused by photodetection of the reflected light 234, and the non-shifted signals, caused by photodetection of the reflected light 232. The low-frequency AC portion of the signal can then be processed to determine the velocity of the blood flow 266 or any vessel wall motion and/or proximate tissue to determine PWV. The Doppler signal energy is typically a distribution of Doppler energy as there are many blood flow contributors of different speeds and angles relative to the source and receiver, for example. The distribution of Doppler energy is then mapped, either analytically, based upon the geometry of the vasculature with respect to the source and receiver and the assumed and/or measured blood velocity profile, or empirically to the correct velocity of 266. The intensity of the DC portion is, in part, related to the presence of a specular reflection between source and detector as it reflects/refracts when it interacts with tissue 251 and vessel 260. The DC portion may be used to detect movement of vessel wall surfaces, for example, when a pulse travels through the interrogated portion of the vessel.

The response signal generated by the reception/photodetection of light by the light detector 230 exhibits an amplitude variation at various depths due to reflection of the received light from a specular reflection of a surface. This amplitude response variation phenomenon can be used to determine the depth 252 of the blood vessel 260 and various features of the blood vessel 260, such as the vessel diameter 262 and the vessel wall thickness 264, for example. The spacing 212 between the light emitter 220 and light detector 230 can be varied to determine the spacing 212 at which the signal response exhibits an increased amplitude due to the presence of a specular reflection of a surface. The depth 252 of the vessel 260 can be determined based in part on the spacings 212 between the light emitter 220 and the light detector 230, where the amplitude response is increased by a specular reflection of the vessel wall, for example. Further, the diameter 262 of the vessel 260 can be estimated by the variance of the spacing 212 between the light emitter 220 and light detector 230 at one or more places of the vessel 260. Additionally, the vessel wall thickness 264 can be estimated from the signal generated by the light emitter 230, in response to the received reflected light 232 and/or 234.

In addition to the amplitude signal, the detector(s) of the light detector 230 along the receive path need to be sufficiently sensitive to detect the Doppler shift in the signal caused by the received reflected light 232, 234, with the Doppler shifted signal likely to be in the few kHz to a few MHz range.

Figure 3:
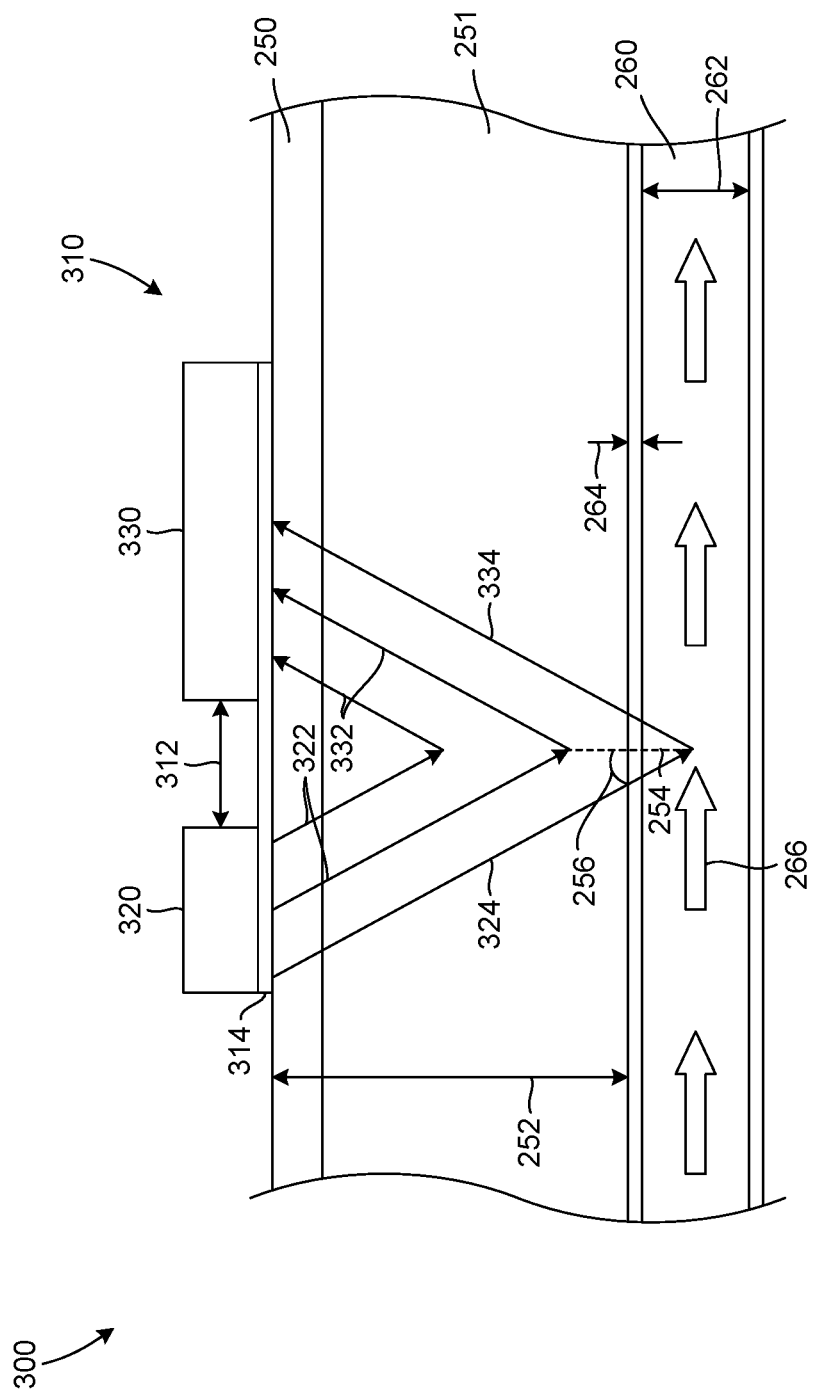
FIG. 3 is an example light-based non-invasive blood pressure system with a non-coherent light source.

FIG. 3 illustrates an example light-based non-invasive blood pressure system 300 with a non-coherent light source. An NIBP sensor 310 is shown, including a light emitter 320, containing a non-coherent light source, and a light detector 330. The light emitter 320 emits light 322 and 324 into tissues, such as tissue 251 and/or blood vessel 260. The light detector 330 receives the reflected light 332 and 334 that is reflected from the tissues of 251 and blood vessel 260. The reflected light 332, 334 is received by the light detector 330 to generate the NIBP signal that can be processed to determine, or can be used to determine, one or more physiological parameters, such as a blood pressure.

In the example of FIG. 3, the non-coherent light source of the light emitter 320 can be a light emitting diode (LED) light source that emits light having a narrow bandwidth. That is the non-coherent light source of the light emitter 320 exhibits narrow bandwidth, non-coherence. Alternatively, the LED light source could also emit light having a broad bandwidth. Unlike the example of FIG. 2, in which the light source is coherent and emits light of known and constant properties, the non-coherent source of the example of FIG. 3 emits light having a range of properties, such as a range of frequencies, wavelengths, periods, phases, and/or other light properties/characteristics. The non-coherent light source has a coherence length, which manifests as a relatively large response at detector 330 when the reference and reflected paths are the same optical length. In the example of a narrow bandwidth, non-coherent source, the coherence length of the emitted light is greater than the coherence length of light emitted by a non-coherent light source emitting light having a broader bandwidth. To account for the coherence length of non-coherent light, the NIBP sensor 310 of FIG. 3 includes a reference path 314 that provides a known pathway for light from the light emitter 320 to detector 330.

The reference path 314 determines the depth to which measurements can be made. The path lengths of the light 322, 324 transmitted through the tissues 251, 260 and back as 332, 334 are limited by the allowable path length of reference light along the reference path 314, which is based on the physical separation between the light source and a detector of the light detector 330. In this manner, the longer the path length of the reference light along the reference path 314, the longer the path length of the light transmission, such as 322, 324, through the tissues and back as 332 and 334 can be. The depth from which measurements can be taken is therefore limited by the allowable path lengths of the light transmissions, such as 322, 324, with reflection 332, 334 from the tissues 251, 260, provided the relative absorption of the light transmitting through the tissues is not so great as to prevent the reflected light 332, 334 from being detected by the light detector 330.

Reference light from the non-coherent light source of the light emitter 320 radiates underneath the emitter 320 and along the reference path 314. The radiated reference light is provided to the detector(s) of the light detector 330 to be mixed with reflected light 332 and 334. In an example embodiment, the reference path 314 can be coated and/or structured so as assist the non-coherent light traveling along the reference path 314 to mix with the reflected light 332, 334. For example, the reference path 314 can be coated such that the portions of the reference path coating under the light detector 330 acts as a one-way mirror, allowing reflected light, such as 332, 334, to pass through the reference path 314 and be received by the light detector 330, while preventing the radiant reference light along the reference path 314 from radiating into the tissues, such as 251, 260. The reference path 314 allows for the mixing of the reflected light 332 and the reference light. This mixing superimposes the reference light emitted from the light emitter 320 and the reflected light 332, 334, which is then detected by/at the light detector 330. In this manner, the process of low-coherence optical interferometry can be used to detect/determine the Doppler shift caused by the light 334 reflecting from the moving blood flow 266 of the vessel 260.

The coherence length of the non-coherent light source determines the "optical slice," range and/or depth, over which a useful interferometric signal can be obtained by the detector, or photodetector, of the light detector 330. The depth at which the measurement is being made, such as the depth from which light is reflected, is based on the path length between the light source and the light detector. The optical slice is the range, at that depth, from which the measurement is being made, such as a ± range about that depth. The coherence length of the non-coherent light determines the breadth of the optical slice or range. In the example narrow bandwidth, non-coherent light source, the optical slice is larger than that of a broader bandwidth, non-coherent light source due to the coherence length of the broader bandwidth, non-coherent light source being shorter than the coherence length of the narrow bandwidth, non-coherent light source.

An example broader, or wide, bandwidth non-coherent light source can include a "white" light source. White light is composed of light having a wide variance of wavelengths, frequencies and/or other properties/characteristics. As such, the coherence length of such light is relatively short and the optical slice is very thin, on the order of microns. This narrow optical slice can increase the accuracy of depth determination since the range, optical slice, is so narrow due to the short coherence length. As such, the use of a wide bandwidth, non-coherent light source can increase the accuracy of the depth determination and/or measurement of various features, such as the depth 252 determination of the blood vessel 260, the diameter 262 of the vessel 260, the wall thickness 264 of the blood vessel and/or other tissue measurements.

In the example system 300 shown in FIG. 3, the spacing 212 between the light emitter 320 and the light detector 330 can be 30 mm, for example, to allow for a penetration depth of the emitted light to be nearly 30 mm deep into the tissues 251, 260. Other example spacing distances can range from 10-100 mm.

In the examples of FIGS. 2 and 3, the NIBP sensor 210, 310 can include multiple light sources emitting light with similar and/or different properties. For example, the light emitter can include multiple sources emitting light having the same properties, multiple sources emitting light having different properties, or a mix of light sources. In this manner, the light emitter and light detector of the NIBP sensor 210, 310 can have multiple pairs of light sources and detectors having varying spacing between them so that physically varying the separation of the light emitter and light detector is not required to alter the depth of sensing. Additionally, as described previously, the light emitter 220/320 can contain one or more light sources that emit light, such as 222/322, 224/324, into the tissue 251 and vessel 260, and the light detector 230/330 can contain one or more detectors to detect reflected light, such as 232/332, 234/334, from tissues/ features of the tissue 251 and vessel 260. That is, the light emitter 220/320 can contain multiple light sources that are arranged to emit light into the tissues 251, 260 and the light detector 230/330 can contain multiple detectors, such as photodiodes, arranged to receive the reflected light. Each of the light sources of the light emitter 220/320 can be arranged to form a pair with a detector of the light detector 230/330, separated by a spacing 212. With this arrangement of light sources of the light emitter 220/320 and detectors of the light detector 230/330, multiple spacings 212 between source and detector pairs can be achieved. The signals from the one or more detectors of the light detector 230/330 can be multiplexed and output as the NIBP signal for processing to determine one or more physiological parameters, such as the instantaneous blood velocity and/or PWV.

To assist with locating a vessel, such as 260, the NIBP module and/or the NIBP sensor can include a manual and/or automatic search algorithm that can prompt the user to alter the spacing of the NIBP sensor and/or can activate one or more light sources of the light emitter to provide NIBP signals from various depths. The NIBP signal(s), associated with a particular light source(s) and/or spacing(s), exhibiting Doppler shift are indicative of the depth at which the vessel is located. The search algorithm can control the activation of the light sources to find the Doppler shifted signal to determine the depth of the vessel, such as 260. The light source-detector pair exhibiting the largest magnitude of the Doppler response can then be selected for use in determining and/or measuring various physiological parameters and/or features. Additionally, differentiation between veins and arteries is possible based on the static or dynamic nature of the Doppler signal from each.

In an example embodiment in which the light detector contains multiple detectors, the signal from each of the detectors can be multiplexed to form a single signal, the NIBP signal, or each signal, or groups of signals, can be assigned an individual channel for processing. That is, the signal from the NIBP sensor having multiple detectors can be a single, multiplexed NIBP signal or can be two or more NIBP signals assigned to individual channels for processing. The use of multiple channels for processing can increase the acquisition rate of the signal and therefore provide increased temporal resolution of the parameters being monitored and/ or measured.

In an example embodiment, the light emitter 320 and/or the light detector 330 can be integrated with another device and/or system and/or the necessary light emission and/or detection can be performed by another device and/or system to generate, or assist with generating, the NIBP signal. For example, the light emitter and/or light detector can be integrated with a light-based pulse oximetry and/or perfusion sensor/system. The other device and/or system can emit light that can be detected by the light detector 330 of the NIBP sensor 310, the other device can detect the light emitted by the light emitter 320 of the NIBP system 310, or both the light emission and detection of the light emitter 320 and light detector 330 can be performed by the other device/system, to generate the NIBP signal for processing.

Figure 4:
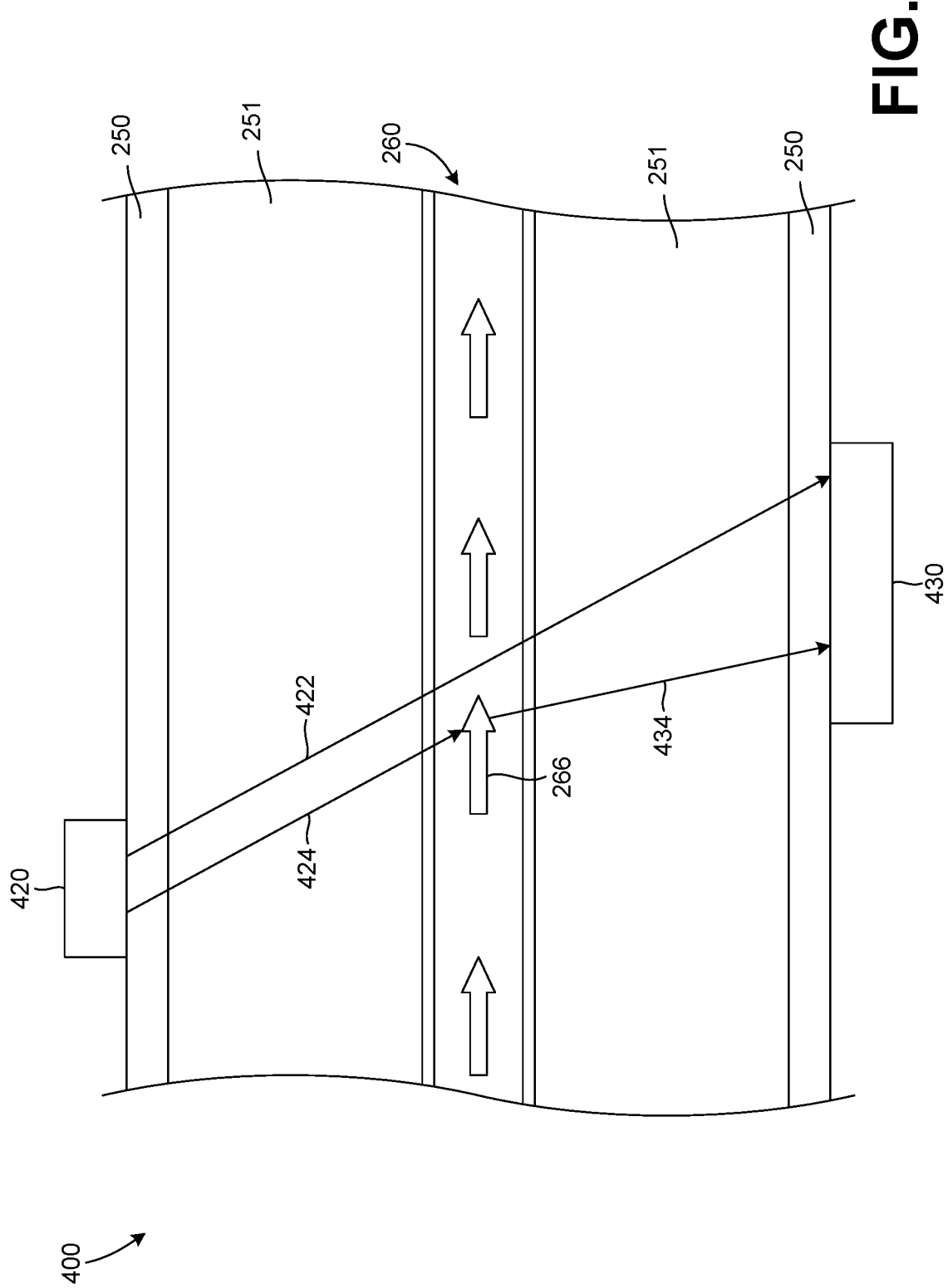
FIG. 4 is an example arrangement of a light-based non-invasive blood pressure system.

FIG. 4 illustrates an example light-based non-invasive blood pressure system 400 that includes an NIBP sensor. The NIBP sensor includes a light emitter 420 and a light detector 430 arranged about one or more tissues. The light emitter 420 emits light 422 and 424 into tissues, such as tissue 250, 251 and/or blood vessel 260. The light detector 430 receives the transmitted light 422, which transmits through the tissues, and reflected, or scattered, light 434 that reflects/ scatters from the blood flow 266. In response to the received light 434 and 422, the light detector 430 generates the NIBP signal that can be processed to determine, or can be used to determine, one or more physiological parameters, such as a blood pressure.

The light emitter 420 and light detector 430 are shown on substantially opposite sides of the tissue cross-section of FIG. 4. In other embodiments, alternative arrangements of the light emitter 420 relative to the light detector 430 are possible. In these various arrangements, the light detector 430 will receive light transmitted through and/or reflected/scattered from the various tissues, such as 250, 251 and 260. The reflected/scattered light received by the light detector 430 causes the NIBP signal to be generated, which can then be processed/analyzed for various calculations/measurements. In an example, the reflected/scattered light 434 from the blood flow 266 exhibits a Doppler response. The Doppler response is part of the generated/output NIBP signal, from which a velocity of the blood flow 266 can be calculated/measured. The velocity measurement can then be used to determine a blood pressure. Doppler responses of the vessel wall and/or proximate tissue can be used to detect pressure pulse motion at one or more places from which pulse wave velocity may be derived.

Figure 5:
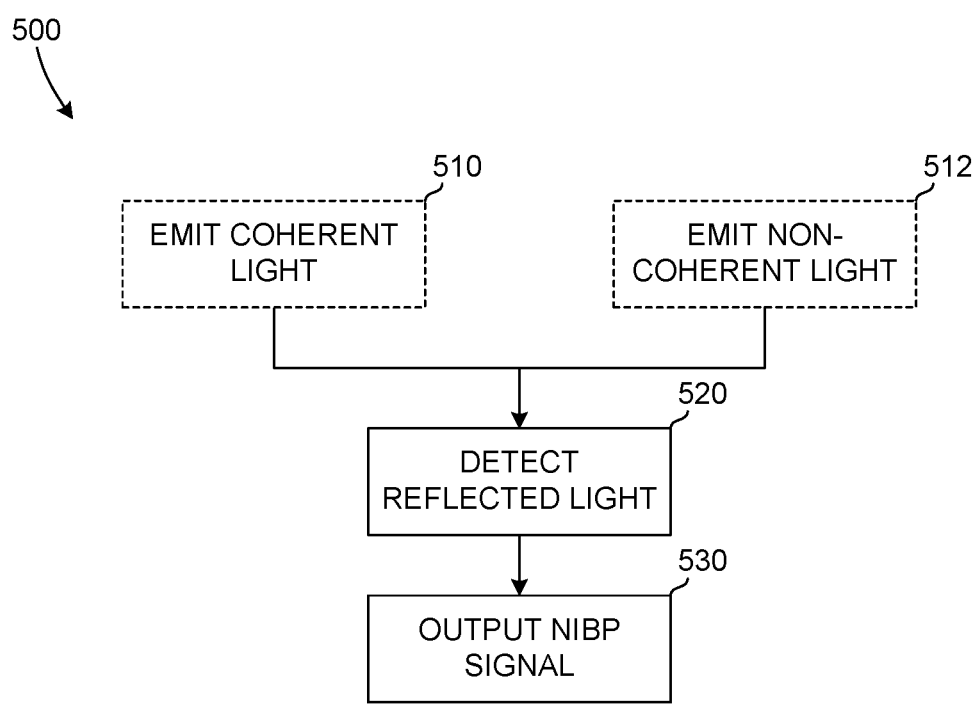
FIG. 5 is an example method of generating a non-invasive blood pressure signal.

FIG. 5 illustrates an example non-invasive blood pressure signal generation method 500. At 510 coherent light is emitted and/or at 512 non-coherent light is emitted, the emitted light is directed into the tissues of a person. The emitted coherent light 510 and/or the emitted non-coherent light 512 can be emitted from one or more light sources of a light emitter, such as previously described. The characteristics/properties of the emitted light can interact with the tissues to cause localized heating of the tissues and/or the heating of the tissues can be caused by the waste heat due to the generation of the emitted light. The heating of the tissues can cause discomfort to a person associated with the tissues and/or can cause damage to the tissues. To reduce and/or minimize the discomfort and/or damage, the intensity of the emitted light can be controlled and/or the duration of light exposure can be controlled. Controlling one or both of the light intensity and the duration of exposure to the light can allow the heating of the tissues to be controlled. For example, a high intensity of light can be emitted for a short duration so as to provide the necessary intensity to transmit light to a required and/or desired depth into the tissues while limiting the duration so as not to unduly heat the tissues exposed to the emitted light.

The light emitted at 510 and/or 512 transmits through the tissues and reflects therefrom. The reflected light is detected at 520, such as by a photodetector/light detector, with the light detector generating a signal in response with the interaction between the reference and the reflected light. The signal output by the detector(s) is the NIBP signal 530. When the light transmitted through the tissues reflects from moving tissues, such as a blood cell of a blood flow through a vessel, the reflected signal has a Doppler shift/frequency that can be detected in the signal. When the light transmitted through the tissues reflects from stationary tissues, such as found in the skin or non-moving tissues outside the vessel, the reflected signal exhibits little to no Doppler shift due to the reflection from a substantially static tissue. The NIBP signal generated at 530 can be analyzed to determine the presence of a Doppler shift/frequency, and if such Doppler frequency is present, it can be analyzed to determine a velocity of the moving tissues, such as the instantaneous velocity of the blood flow through the vessel or to detect motion of the blood vessel wall and/or proximate tissue. If the NIBP signal generated at 530 is analyzed and there is not an indication of a Doppler shift/frequency, such as might be caused by the reflection from a moving tissue, then one or more parameters of the light emission and/or light detection can be altered to cause the emitted light to contact and reflect from moving tissues, such as the blood flow through the vessel, in order to obtain an NIBP signal containing the Doppler shifted signal. The Doppler shifted NIBP signal can be processed, such as using a method 600 of FIG. 6, to determine one or more physiological parameters and/or characteristics of the patient/person.

Figure 6:
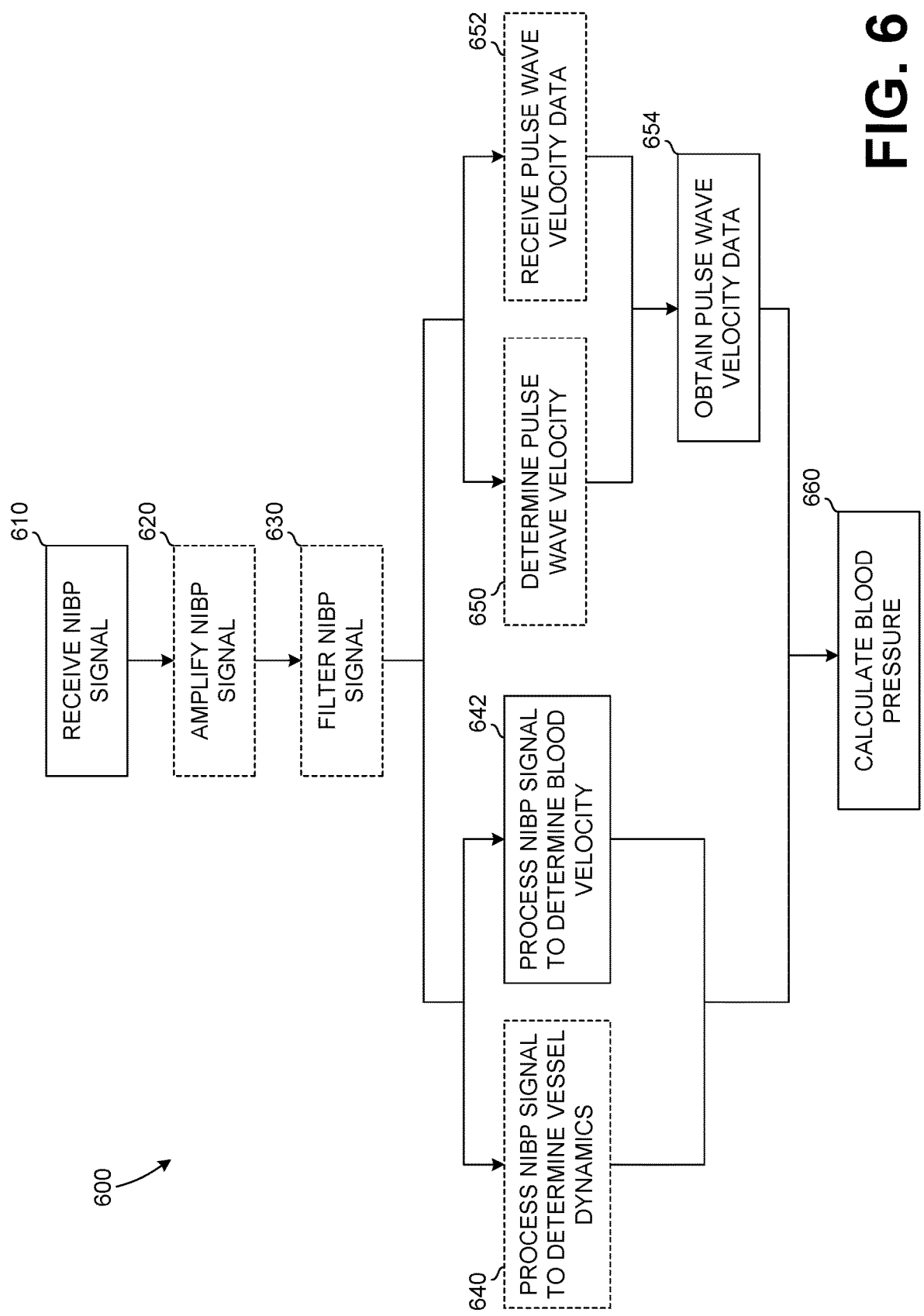
FIG. 6 is an example method of determining a non-invasive blood pressure.

FIG. 6 illustrates an example non-invasive blood pressure method 600. At 610, the NIBP signal is received, such as by an NIBP module from an NIBP sensor. At 620, the NIBP signal can be amplified, optionally, such as by passing the signal through a low-noise amplifier and/or circuit. The NIBP signal can then be filtered, optionally, at 630. The filtering at 630 can include anti-alias filtering of the NIBP signal and the conversion of the analog NIBP signal to a digital signal, such as by the use of an analog-to-digital converter (ADC).

As discussed above, the Doppler shift of the NIBP signal is the AC response of the NIBP signal, so the NIBP signal can be further filtered at 630 to remove the DC response, in some examples. The removal of the DC response of the NIBP signal can be done using a high pass filter (HPF) and/or a band pass filter (BPF) to remove the portion of the signal associated with the DC response. If the bandwidth is sufficiently low, the sample rate of the NIBP signal can be decimated, if required and/or desired.

At 640 and/or 642, the NIBP signal can be processed to determine vessel dynamics, such as at 640, and/or to determine an instantaneous blood velocity, such as at 642. To determine the instantaneous blood velocity associated with the Doppler data of the NIBP signal, the Doppler spectrum of the NIBP signal can also be scaled, as previously described, by correcting the spectrum by the incidence and reflection angles as measured with respect to the motion being detected, i.e., the blood flow. The angle(s) can be value(s) that a user inputs, value(s) that are assumed by the processing of the signal and/or determined from one or more scans of the vasculature/tissue. The NIBP Doppler data as a function of depth can be used to determine the cross-section, or diameter, of the blood vessel as a function of time.

At 650 and/or 652, pulse wave velocity data is determined/received at near, or substantially, simultaneously as the determination of the blood velocity. Substantially simultaneously is at a time recent enough to be the PWV that would have been measured coincident with blood velocity, which could be some time later. Alternatively, the PWV could be averaged or taken a time separate from the determination of the blood velocity, such as an average of the patient's historical PWV over time (e.g., minute(s), hour(s), day(s), or even month(s)). While the preference may be to rely on a PWV that is as temporally near the determination of the blood velocity as reasonably possible, the patient's historical data can also be used in applications that do not require as much accuracy or precision, such as fitness testing, non-emergency or non-critical medical situations, and the like.

At 650, the pulse wave velocity can be determined, such as from data and/or measurements received/obtained by the NIBP system, such as by the sensors/system of the NIBP system, including an NIBP sensor and/or NIBP module. For example, CWD techniques can be used to determine PWV data using the light emitter and light detector of the NIBP system. Collection of PWV data can occur nearly, or substantially, simultaneously as the acquisition of the NIBP signal by the NIBP system. In an example, PWV data can also be obtained and/or determined from the NIBP signal. At 652, the pulse wave velocity data needed for further processing to determine a blood pressure, can be received from an external system, device and/or user. Example external systems/device for obtaining the pulse wave velocity can include the use of ultrasound based devices/systems, light based devices/systems and/or pressure/motion sensing based devices/systems. The external system/device can capture the PWV data at near, or substantially, simultaneously as the acquisition of the NIBP and/or determination of the blood velocity. The near, or substantially, simultaneous acquisition of the blood velocity and PWV provides the necessary information to calculate blood pressure, such as by Equation 1, without a calibration step. At 654 the PWV data is obtained, from one or both of 650, 652, for use in determining/calculating the blood pressure.

At 660, the blood pressure of the patient can be calculated and/or determined using the pulse wave velocity data from 650, 652 and the instantaneous blood velocity and/or vessel dynamics data from 640, 642. For example, the instantaneous blood velocity data of 642, the pulse wave velocity data of 652 and the assumed constant density of blood, can be processed using Equation 1 to determine the blood pressure of the patient based on the foregoing parameters/measurements.

Additionally, the data derived and/or generated from the NIBP system can be used to assess various cardiac performance parameters. Using the blood vessel velocity profile and the blood velocity measurement and the vessel diameter and/or area from the NIBP system, the blood volume per unit time can be calculated/determined, including net flow by integrating over time. The net flow can indicate reverse flow within the cardiac cycle and can also be used in the calculation of various other cardiac performance parameters such as cardiac output and blood volume flow rate. This and/or other data of the NIBP system, or derived therefrom, can be used in conjunction with physiological parameter data from other systems and/or devices to monitor, treat and/or evaluate a patient and/or their physiological performance.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A blood pressure measurement system for measuring blood pressure in a patient without restricting blood flow, comprising:
    an emitter configured to emit light towards blood flowing through a blood vessel;
    a detector configured to:
        detect reflected light that is reflected from the blood flowing through the blood vessel, a frequency of the reflected light being different than a frequency of the light emitted by the emitter;
    and a processor electrically coupled to the detector, the processor being configured to:
        determine an instantaneous blood velocity of the blood flowing through the blood vessel from the frequency of the reflected light;
        receive data indicating a pulse wave velocity of the blood vessel; and
        determine a blood pressure from the instantaneous blood velocity and the pulse wave velocity using the equation:

$P_i = \rho PWV v_i$ wherein $P_i$ is the blood pressure, $\rho$ is a density of the blood, PWV is the pulse wave velocity, and $v_i$ is the instantaneous blood velocity.

2. The blood pressure measurement system of claim 1, further comprising:
    a blood pressure sensor comprising the emitter and the detector; and
    a computing device that is coupled to the blood pressure sensor by a wired connection or a wireless connection, the computing device comprising the processor.

3. The blood pressure measurement system of claim 1, wherein the blood pressure comprises a beat-to-beat blood pressure.

4. The blood pressure measurement system of claim 1, wherein the emitter comprises a coherent light source.

5. The blood pressure measurement system of claim 1, wherein the emitter comprises a non-coherent light source.

6. The blood pressure measurement system of claim 1, wherein the emitter comprises a laser diode.

7. The blood pressure measurement system of claim 1, wherein the emitter comprises laser diodes that are configured to emit light having different frequencies.

8. The blood pressure measurement system of claim 1, wherein the detector comprises a photodiode.

9. The blood pressure measurement system of claim 1, further comprising:
    a pulse wave velocity element configured to detect the pulse wave velocity of a pressure wave travelling down the blood vessel.

10. The blood pressure measurement system of claim 9, wherein the pulse wave velocity element is configured to detect the pulse wave velocity substantially simultaneously as the detector detects the reflected light.

11. The blood pressure measurement system of claim 9, wherein the pulse wave velocity element comprises an ultrasound sensor, a pressure sensor, a motion sensor, or a high-resolution optical sensor.

12. The blood pressure measurement system of claim 1, the reflected light being first reflected light, wherein the detector is further configured to detect second reflected light that is reflected from the blood vessel or tissue surrounding the blood vessel,
    wherein the processor is further configured to determine a characteristic of the blood vessel based on the second reflected light, and
    wherein the characteristic comprises a depth of the blood vessel, a diameter of the blood vessel, a wall thickness of the blood vessel, or a wall elasticity of the blood vessel.

13. The blood pressure measurement system of claim 1, further comprising a display electrically coupled to the processor and configured to display the blood pressure.

14. The blood pressure measurement system of claim 1, further comprising a communication module electrically coupled to the processor and configured to transmit data indicating the blood pressure, the instantaneous blood velocity, or the pulse wave velocity to a remote computing device.

15. A blood pressure measurement system comprising:
    a blood pressure sensor comprising:
        an emitter configured to emit light towards blood flowing through a blood vessel;
        a detector configured to detect the light reflected from the blood flowing through the blood vessel, a frequency of the light reflected from the blood flowing through the blood vessel being different than a frequency of the light emitted by the emitter; and a processor configured to:
  determine an instantaneous blood velocity of the blood flowing through the blood vessel from the frequency of the light reflected from the blood flowing through the blood vessel;
  identify a pulse wave velocity of a pulse traveling along the blood vessel; and
  determine a blood pressure from the instantaneous blood velocity and the pulse wave velocity using the equation:

$$P_i = \rho PWV v_i$$

wherein $P_i$ is the blood pressure, $\rho$ is a density of the blood, PWV is the pulse wave velocity, and $v_i$ is the instantaneous blood velocity.

16. The blood pressure measurement system of claim 15, wherein the blood pressure sensor comprises a patch configured to be affixed to a patient.

17. The blood pressure measurement system of claim 15, further comprising:
  a computing device that comprises the processor,
  wherein the blood pressure sensor further comprises a transmitter configured to transmit, to the computing device, data indicating the light reflected from the blood flowing through the blood vessel.

18. The blood pressure measurement system of claim 15, the emitter being a first emitter configured to emit first light, the blood pressure measurement system further comprising:
  a second emitter configured to emit second light towards the blood vessel or the blood flowing through the blood vessel,
  wherein the detector is configured to detect the first light reflected from the blood flowing through the blood vessel and to detect the second light reflected from the blood vessel or the blood flowing through the blood vessel.

19. The blood pressure measurement system of claim 15, the detector being a first detector, the blood pressure measurement system further comprising:
  a second detector configured to detect the light reflected from the blood flowing through the blood vessel.

20. A blood pressure measurement system comprising:
emitters configured to emit light towards blood flowing through a blood vessel;
detectors configured to detect light reflected from the blood flowing through the blood vessel, a frequency of the light reflected from the blood flowing through the blood vessel being different than a frequency of the light emitted by the emitters; and
a processor configured to:
  determine an instantaneous blood velocity of the blood flowing through the blood vessel from the frequency of the light reflected from the blood flowing through the blood vessel;
  identify a pulse wave velocity of a pulse traveling along the blood vessel; and
  determine a blood pressure from the instantaneous blood velocity and the pulse wave velocity using the following equation:

$$P_i = \rho PWV v_i$$

wherein $P_i$ is the blood pressure, $\rho$ is a density of the blood, PWV is the pulse wave velocity, and $v_i$ is the instantaneous blood velocity.

21. The blood pressure measurement system of claim 20, wherein the emitters comprise a first emitter configured to emit first light and a second emitter configured to emit second light,
  wherein the detectors comprise a first detector configured to detect the first light reflected from the blood vessel or the blood flowing through the blood vessel and a second detector configured to detect the second light reflected from the blood vessel or the blood flowing through the blood vessel, and
  wherein a spacing between the first emitter and the first detector is different than a spacing between the second emitter and the second detector.

* * * * *